(12) United States Patent
Basara

(10) Patent No.: US 7,115,251 B2
(45) Date of Patent: Oct. 3, 2006

(54) METHOD FOR EXFOLIATING SKIN

(75) Inventor: Michael Basara, Hugo, MN (US)

(73) Assignee: Northern Research Laboratories, Inc., Saint Paul, MN (US)

( * ) Notice: Subject to any disclaimer, the term of this patent is extended or adjusted under 35 U.S.C. 154(b) by 245 days.

(21) Appl. No.: 10/443,445

(22) Filed: May 21, 2003

(65) Prior Publication Data

US 2004/0234490 A1    Nov. 25, 2004

(51) Int. Cl.
*A61K 7/00*   (2006.01)
*A61K 9/00*   (2006.01)

(52) U.S. Cl. .................. 424/47; 424/400; 424/59; 424/70.8

(58) Field of Classification Search .............. 424/401, 424/400, 43, 45, 47, 59, 63, 70.1, 70.8, 70.9, 424/70.24, 78.03
See application file for complete search history.

(56) References Cited

U.S. PATENT DOCUMENTS

| | | | |
|---|---|---|---|
| 3,459,800 A | | 8/1969 | Salat et al. |
| 3,920,835 A | | 11/1975 | Van Scott et al. |
| 3,984,556 A | | 10/1976 | Hardtmann |
| 3,988,470 A | | 10/1976 | Van Scott et al. |
| 4,080,212 A | | 3/1978 | Takahashi |
| 4,082,841 A | | 4/1978 | Pader |
| 4,144,325 A | * | 3/1979 | Voyt ............................ 424/59 |
| 4,416,982 A | | 11/1983 | Tsuda et al. |
| 5,688,995 A | * | 11/1997 | Luther et al. ................. 562/30 |
| 6,596,299 B1 | | 7/2003 | Basara |
| 6,830,757 B1 | | 12/2004 | Basara |

FOREIGN PATENT DOCUMENTS

| | | |
|---|---|---|
| GB | 820659 | 9/1959 |
| WO | WO-2004062580 A3 | 7/2004 |

OTHER PUBLICATIONS

Budavari, et al., *The Merck Index, eleventh edition*, (1989), p. 7212.
Forstner, J. , et al., "Intestinal goblet cell mucus: isolation and identification by immunofluorescence of a goblet cell glycoprotein", *J Cell Sci.*, 12(2), (Mar. 1973),585-602.
Lebat-Robert, J. , et al., "Glycoproteins du mucus gastrique: structure, fonctions et pathologie", *Pathologie biologie*, 24, (1979),241-247.
Lehr, C. M., et al., "Visualization studies of the mucoadhesive interface", *Journal of Controlled Release*, 18, (1992),249-260.
Peppas, N. , et al., "Suface, interfacial and molecular aspects of polymer bioadhesion on soft tissues", *Journal of Controlled Release*, 2, (1985),257-275.
Spiro, R. G., "Glycoproteins", *Annu Rev Biochem.*, 39, (1970),599-638.

* cited by examiner

*Primary Examiner*—Dameron L. Jones
(74) *Attorney, Agent, or Firm*—Schwegman, Lundberg, Woessner & Kluth, P.A.

(57) ABSTRACT

The present invention relates to an exfoliating composition. The composition comprises a mixture. The mixture comprises phenolsulfonic acid, guaiacolsulfonic acid, and optionally sulfosalicylic acid and citric acid.

13 Claims, No Drawings

METHOD FOR EXFOLIATING SKIN

Reference is made to the following commonly assigned application entitled as follows: ODORLESS FORMULATION FOR TREATING MUCOSAL DISCONTINUITIES. The above-identified Application being filed on May 21, 2003, the same filing date as the instant application.

BACKGROUND OF THE INVENTION

The present invention relates to a method for exfoliating skin, including facial skin, skin on the bottom of feet, and elbows.

Skin atrophy refers to a thinning or general degradation of the dermis layer of mammalian skin. Skin atrophy is often characterized by a decrease in collagen and elastin. Skin atrophy is a natural result of aging, but may be caused by either intrinsic or extrinsic factors such as natural chronological aging, photo damage, burns or chemical damage, or by exposure to pollutants or allergens such as cigarette smoke. Skin atrophy is an undesirable side effect resulting from treatment with alpha hydroxy carboxylic acids.

On the opposite end of the spectrum are corns and callouses. Corns and callouses are hard skin that develops when skin is exposed to excessive pressure or friction. A corn is hard skin with a small core that includes tissue that is as hard as bone or nail. Corns and callouses are typically treated with abrasive materials and abrasive devices.

Cosmetic compositions that include alpha or beta hydroxy acid, AHA/BHA as the active ingredient, are well-known in the art. These compositions are useful in improving skin tone, reduction of fine lines, enhancement of moisture, and development of smooth skin. Application of AHA/BHA results in younger looking skin as new cells replace the old. Unfortunately, the AHA/BHA acts most effectively at low pH conditions. In order to improve skin condition, users must tolerate skin irritation caused by the acid present in the AHA/BHA products. Skin irritation is a major concern then, to manufacturers and users to these products.

SUMMARY OF THE INVENTION

One embodiment of the present invention is an exfoliating composition. The exfoliating composition comprises a mixture comprising phenolsulfonic acid, guaiacolsulfonic acid and, optionally, sulfosalicylic acid.

Another embodiment of the present invention includes a method for exfoliating skin, comprising: cleansing skin that is to be exfoliated; providing an exfoliating composition comprising phenolsulfonic acid, guaiacolsulfonic acid and, optionally, sulfosalicylic acid; and applying the exfoliating composition to skin which has been cleansed for a time effective to exfoliate the skin.

Another embodiment of the present invention includes a method for making an exfoliant, comprising: blending a mixture of one or more phenolsulfonic acid, guaiacolsulfonic acid, sulfosalicylic acid, and citric acid in amounts effective to exfoliate skin.

One other embodiment of the present invention includes a device comprising: the formulation of the present invention and a container for enclosing and transporting the formulation.

DETAILED DESCRIPTION

One embodiment of the present invention includes a method for exfoliating skin. The method comprises exposing skin, which has been cleansed, to a solution or a cream or lotion or paste or gel or foam comprising one or more of sulphonated phenolic compounds including phenolsulfonic acid, guaiacolsulfonic acid, and sulfosalicylic acid, for a time effective to warm the skin and produce a tingling sensation. The solution or cream or paste or gel or foam comprises a mixture of phenolsulfonic acid and one or more of guaiacolsulfonic acid and sulfosalicylic acid. Some embodiments optionally include free acid. In one embodiment, the mixture includes:

| Component | Concentration Ranges |
| --- | --- |
| Phenolsulfonic Acid | 25–80% by weight |
| Guaiacolsulfonic Acid | 25–80% by weight |
| Ammonium Phenolsulfonate | 0–5% by weight |
| Free Sulfuric Acid | 0–3% by weight |
| Water | 13–30% by weight |
| Colorant | 0.075–0.020% by weight |

One exfoliant of the present invention includes two isomers of phenolsulfonic acid and four isomers of guauacolsulfonic acid. Water is added as a diluent in this formulation. Another exfoliant of the present invention additionally includes sulfosalicylic acid. One other exfoliant embodiment includes citric acid. An embodiment used as a foot exfoliant includes ammonium phenolsulfonate and zinc phenolsulfonate. These embodiments include water or alcohol or a mixture of water and alcohol as a diluent.

It is believed that the exfoliant formulations of the present invention macerate the stratus corneum without penetrating into the underlying skin tissue. The exfoliant produces a precipitation reaction that cleanses the skin, particularly lesions on the surface of the skin, without damaging underlying layers. The cleansing aids in repair of the lesions and in the growth of new skin.

One specific embodiment of the solution has the following concentration ranges:

| Component | Concentration Ranges |
| --- | --- |
| Phenolsulfonic Acid | 25–80% by weight |
| Guaiacolsulfonic Acid | 25–80% by weight |
| Ammonium Phenolsulfonate | 0–32% by weight |
| Free Sulfuric Acid | 0–32% by weight |
| Water | 13–30% by weight |
| Colorant | 0.000–0.075% by weight |

Another formulation embodiment is as follows:

| Component | Concentration Ranges |
| --- | --- |
| Phenolsulfonic Acid | 25–80% by weight |
| Guaiacolsulfonic Acid | 25–80% by weight |
| Ammonium Phenolsulfonate | 0–5% by weight |
| Free Sulfuric Acid | 0–3% by weight |
| Water | 13–30% by weight |
| Colorant | 0.000–0.075% by weight |

As used herein, "Exfoliation" refers to a detachment and shedding of superficial cells of an epithelium or from any tissue surface. Tissue surfaces include but are not limited to facial skin, skin on the soles of feet, knees, elbows, legs, arms, and other skin areas. Exfoliation also includes detachment or shedding of calloused skin, such as skin on the sole and heel of a foot, skin on an elbow and callouses on other parts of the body.

"Pharmaceutical" refers to a formulation administered to the skin which renders a benefit or an effect for treating or preventing an abnormal biological condition or a disease.

"Skin Atrophy" refers to a thinning and/or a general degradation of the dermis layer of mammalian skin, often characterized by a degree in collagen and/or elastic, as well as a doubling of fibroblast cells. Skin atrophy is a natural result of the aging process, but may be caused by either intrinsic or extrinsic factors such as photo damage, burns or chemical damage, or by exposure to pollutants or allergens such as cigarette smoke. Skin atrophy is often an undesirable side-effect resulting from treatment with alpha hydroxy carboxylic acids.

One embodiment of the present invention includes an exfoliation composition. The exfoliation composition of the present invention includes creams, gels, foams and pastes. The formulation includes a diluent such as water, aqueous alcohol, glycol or other inactive carrier which includes up to about 4 percent sulfonated phenol exfoliating material. The exfoliation material, intended for topical application includes, for some embodiments, carrier, excipient, or vehicle ingredients such as, for example, water, acetone, ethanol, ethylene glycol, propylene glycol, butane-1,3 diol, isopropyl myristate, isopropyl palmitate, mineral oil and mixtures thereof to form lotions, tinctures, creams, emulsions, gels, or ointments which are non-toxic and pharmaceutically, cosmetically or dermatologically acceptable. Additionally, moisturizers or humectants are added to the present composition, if desired.

In addition to the diluent, formulations of the sulfonated phenols also, for some embodiments, include other standard adjuvants such as an emollient, moisturizer, thickener, emulsifier, neutralizer, coloring agent, UV absorber or filter, preservative and or gelling agent. When employed in a formulation, these adjutants are present in amounts ranging from about 0.5% to 30%.

Emollient

Acceptable emollients include saturated fatty acids such as isopropyl myristate, cetyl palmitate and octyldodecylmyristate, beeswax, saturated and unsaturated fatty alcohols such as behenyl alcohol and cetyl alcohol, hydrocarbons such as mineral oils, petrolatum, squalene, fatty sorbitan esters, lanolin and lanolin derivatives, such as lanolin alcohol ethoxylated, hydroxylated and acetylated lanolins, cholesterol and derivatives thereof, animal and vegetable triglycerides such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil and diisostearylmalate, diisostearyldimerate and triisostearyltrimerate.

Suitable emollients for use herein include isocetyl alcohol, octyl palmitate, isostearyl neopentanoate and isocetyl stearyl stearate, natural or synthetic oils selected from mineral, vegetable, and animal oils, fats and waxes, fatty acid esters, fatty alcohols, alkylene glycol and polyalkylene glycol ethers and esters, fatty acids and mixtures thereof.

Emulsifier

Suitable emulsifiers include glyceryl stearate and laureth 23, PEG 20 stearate, and mink-amidopropyl dimethyl 2-hydroxyethylammonium chloride.

Typical moisturizers used in the formulation of the present invention include glycerin, petrolatum and maleated vegetable oil.

The sulphonated phenolic material is formulated, in some embodiments, with a gelling agent. Suitable gelling agents include water soluble or colloidally water soluble polymers and include cellulose ethers, such as hydroxyethyl cellulose, methyl cellulose, hydroxypropylmethyl cellulose, polyvinylalcohol, polyquaternium-10, guar gum, hydroxypropyl guar gum and xanthan gum. Other gelling agents usable the present invention include acrylic acid/ethyl acrylate copolymers and carboxyvinyl polymers. Also usable are maleic anhydride-alkyl methylvinylethers and copolymers, natural gums, and polymethacrylate copolymer. Other suitable gelling agents include oleogels such as trihydroxystearin and aluminum magnesium hydroxy stearate.

Some embodiments of the formulation of the present invention include preservatives. The preservatives include sodium benzoate and propyl paraben and mixtures of these materials. Other additional materials include fragrances, fillers such as nylon, sun screens, electrolytes such as sodium chloride, proteins, antioxidants and chelating agents, and ultraviolet absorbing agents. The ultraviolet absorbing agents include benzophenone-3, benzophenone-4, oxytyl dimethyl PABA (Padimate O), octyl methoxy cinnamate, octyl salicylate, octocrylene, p-methylbenzylidene camphor, butyl methoxy dibenzoyl methane, titanium dioxide, zinc oxide and mixtures of these materials.

The exfoliant compositions of the present invention are believed to enhance cell renewal, skin smoothing, exfoliation of calloused skins, removal of skin blemishes, reduction in corn size, and in toning skin.

In addition to these and other vehicles which are selected by those being skilled in the art, it is understood that pharmaceutical and cosmetic compositions of the present invention include other ingredients such as, for example, not by way of limitation, those that improve or eradicate age spots, keratosis and wrinkles; analgesics; anaesthetics; anti-acne agents; anti-bacterial, anti-yeast agents, anti-fungal agents, anti-viral agents, anti-dandruff agents, anti-dermatitis agents, anti-pruritic agents, anti-metic agents, anti-inflammatory agents, anti-hyperkeratolytic agents, anti-dry skin agents, anti-perspirants, anti-psoriatic agents, anti-seborrheic agents, hair conditioners and hair treatment agents, anti-aging and anti-wrinkle agents, skin-whitening agents, de-pigmenting agents, vitamins, tanning agents, hormones, retinoids, vitamin A palmitate and vitamin E acetate.

The present invention also includes methods for enhancing epidermal exfoliation and/or enhancing epidermal skin renewal. The method includes topically administering to an area of a subject's skin, an effective amount of a composition of the present invention for a period of time effective to enhance epidermal exfoliation and/or enhance epidermal skin renewal.

The present invention also provides methods for improving the texture and/or appearance of skin. The method comprises administering to an area of a subject's skin, an effective amount of the exfoliant of the present invention for a period of time effective to improve the texture and/or appearance of skin. In one embodiment, the application time is within a range of thirty seconds to thirty minutes.

The present invention also provides methods for treating or preventing an abnormal skin condition, disease or disorder. The methods comprise administering to an area of a subject's skin an effective amount of the exfoliant of the present invention which comprises two isomers of phenolsulfonic acid, four isomers of guaiacolsulfonic acid and, optionally, sulfosalicylic acid for a period of time effective to treat or prevent an abnormal skin condition, disease, or disorder. The time range is thirty seconds to thirty minutes.

The condition, disease or disorder includes, but is not limited to, dry skin, severe dry skin, dandruff, acne, keratosis, eczema, skin flakiness, age spots, hyper-pigmented skin, inflammatory dermatosis, age-related skin changes, skin in need of cleansers, and the effects of skin atrophy and psoriasis.

One method of administration of an effective amount of the exfoliant of the present invention for any of the methods described herein is when on an area of skin by a topical application. The amount of the exfoliant and frequency of topical application to the skin varies widely, depending upon factors such as the particular skin disorder, the severity of the skin disorder, the location and/or type of skin involved, the subject's skin sensitivity, and the degree of treatment desired. It is well within the purview of the skilled artisan to administer regular dosages according to a subject's need. It is suggested as an example that daily application range from about once per week to about one time per day.

Another mode of administration is a chronic administration. Chronic administration has a duration of months to years. Chronic administration also ranges from about once per week to once per day.

A kit embodiment for treatment of callouses on feet or other body part, includes the exfoliation formulation of the present invention, a container for the formulation and a device for abrading a callous after the exfoliation formulation is applied. The device includes one or more of an abrasive pad, a brush, an abrasive board, or other abrasive device.

Some embodiments of the exfoliant are applied in spas, salons, or other facilities specializing in skin care. Other embodiments are applied in the home by a purchaser. Some embodiments of the exfoliant are sold in drug stores, grocery stores, and department stores.

While specified embodiments of the invention have been herein described, it is to be appreciated that various changes, rearrangements and modifications may be made therein without departing from the scope of the invention as defined by the appended claims.

What is claimed is:

1. An exfoliating composition comprising: a mixture comprising phenolsulfonic acid, guaiacolsulfonic acid, and sulfosalicylic acid in a concentration effective for exfoliating human skin.

2. The exfoliating composition of claim 1, further comprising one or more of an emollient, a moisturizer, a thickener, and emulsifier, a neutralizer, a coloring agent, and UV absorber or filter, and a preservative.

3. The exfoliating composition of claim 1 wherein the mixture is a liquid solution.

4. The exfoliating composition of claim 1 wherein the mixture is a gel.

5. The exfoliating composition of claim 1 wherein the mixture is a cream or paste or foam.

6. The exfoliating composition of claim 1 wherein the mixture has a pH within a range of 2 to 6.

7. The exfoliating composition of claim 1 wherein the phenol sulfonic acid has a concentration up to at least about 24% by volume of the mixture.

8. The exfoliating composition of claim 1 wherein the phenol sulfonic acid concentration is about 4% by volume of the mixture.

9. The exfoliating composition of claim 1, further comprising citric acid.

10. A device comprising the formulation of claim 1 and a container for enclosing and transporting the formulation.

11. The device of claim 10, further comprising a mechanism for dispensing the formulation.

12. The device of claim 10, further comprising a mechanism for heating or cooling the formulation.

13. The device of claim 10, further comprising an applicator.

* * * * *